United States Patent [19]

Bellows

[11] Patent Number: 4,822,744

[45] Date of Patent: Apr. 18, 1989

[54] SYSTEM AND METHOD FOR DETECTING CONTAMINANTS IN A STEAM POWER GENERATING SYSTEM

[75] Inventor: James C. Bellows, Maitland, Fla.

[73] Assignee: Westinghouse Electric Corp., Pittsburgh, Pa.

[21] Appl. No.: 44,623

[22] Filed: May 1, 1987

[51] Int. Cl.$^4$ .............................................. G01N 27/00
[52] U.S. Cl. ....................................... 436/38; 422/68; 422/70; 422/83; 422/89; 436/110; 436/119; 436/125; 436/126; 436/149; 436/150; 436/161
[58] Field of Search ................. 436/38, 125, 103, 110, 436/119, 124, 126, 149, 150, 161; 422/68, 70, 83, 89

[56] References Cited

U.S. PATENT DOCUMENTS

| | | | |
|---|---|---|---|
| 3,158,444 | 11/1964 | Larson et al. | 422/76 X |
| 3,904,365 | 9/1975 | Larson et al. | 422/81 X |
| 4,251,219 | 2/1981 | Larson et al. | 436/125 X |
| 4,251,220 | 2/1981 | Larson et al. | 436/125 X |
| 4,283,200 | 8/1981 | Bodmer et al. | 436/125 |
| 4,472,354 | 9/1984 | Passell et al. | 436/161 X |
| 4,622,306 | 11/1986 | Diive | 436/150 |

Primary Examiner—Barry S. Richman
Assistant Examiner—Jill Johnston
Attorney, Agent, or Firm—D. C. Abeles

[57] ABSTRACT

Method for monitoring changes in contaminant concentration levels between a feedwater inlet and a steam outlet in a steam generating system and system for detecting sources of contaminants in a steam generating system. The method includes a reliable means for detecting organic contaminants, chlorides, sulfides and nitrides. The invention also includes a method for determining whether the organic compounds are chlorinated, sulfinated or nitrogenated. The method is based on monitoring of ion concentration levels and cation exchanged conductivities in samples of feedwater and steam.

15 Claims, 3 Drawing Sheets

SYSTEM AND METHOD FOR DETECTING CONTAMINANTS IN A STEAM POWER GENERATING SYSTEM

FIELD OF THE INVENTION

This application relates in general to steam generating systems and in particular to a system for detecting contaminants in a steam generating system and identifying sources of such contaminants.

BACKGROUND OF THE INVENTION

Under preferred operating conditions steam generators, such as, for example, the type used in turbo-electric power generation systems, require feedwater which is virtually free of dissolved salts and organic contaminants. This is necessary in part because halide ions, e.g. chlorides, will attack the oxide layer of stainless steel components in the power system resulting in pitting and corrosion of precision machinery. Furthermore, at steam generator temperatures organic compounds react with water and steam to form carboxylic acids and carbonic acid. While the chemical effects of these relatively weak acids on the power generating system are only partially known, their presence does interfere with efforts to detect strong acids such as hydrogen chloride. Unfortunately, the potential sources of organic compounds in a steam power generating system are numerous and are often discovered only after considerable research. Moreover, the presence of chlorinated hydrocarbons in steam generators results in a compound problem wherein the organic matter reacts to form both hydrogen chloride and weak acids. Because the weak acids influence monitoring of newly formed chloride ions, chlorinated organic compounds may be an undetected source of damage.

In the past, steam generating systems have been monitored in order to determine whether dissolved salts and organic compounds are present in the steam, but it is not believed that any effort has been made to distinguish contaminants formed by chemical breakdown in the steam generator system from contaminants otherwise present in the feedwater. For example, in order to identify the source of a newly discovered corrosion contaminant, e.g. a chloride, it is desirable to know whether the contaminant came into the system through the feedwater without change in chemical form or resulted from the reaction of organic matter with steam water.

SUMMARY OF THE INVENTION

Among the several objects of the present invention may be noted a simple method for monitoring changes in contaminant concentration levels between a feedwater inlet and a steam outlet in a steam generating system and a system for detecting sources of contaminants in a steam generating system which overcomes the above discussed disadvantageous or undesirable features, as well as others, of the prior art; the provisions of such method including a more reliable means for detecting organic chloride contaminants than heretofore known in the art; the provisions of such method including a means for determining whether contaminants in a steam generating system result from chemical reaction within the generating system itself or are otherwise present in the incoming feedwater.

In general, there is provided a method for detecting contaminants and the sources of contaminants in a steam generating system. Also in general there is provided an instrumentation system comprising first and second hydrogen cation conductivity monitors and first and second chloride monitors, the first hydrogen cation conductivity monitor and the first chloride monitor being positioned to monitor samples of feedwater and the second hydrogen cation conductivity monitor and the second chloride monitor being positioned to monitor samples of steam.

DETAILED DESCRIPTION OF THE PREFERRED EMBODIMENTS

Figure 1:
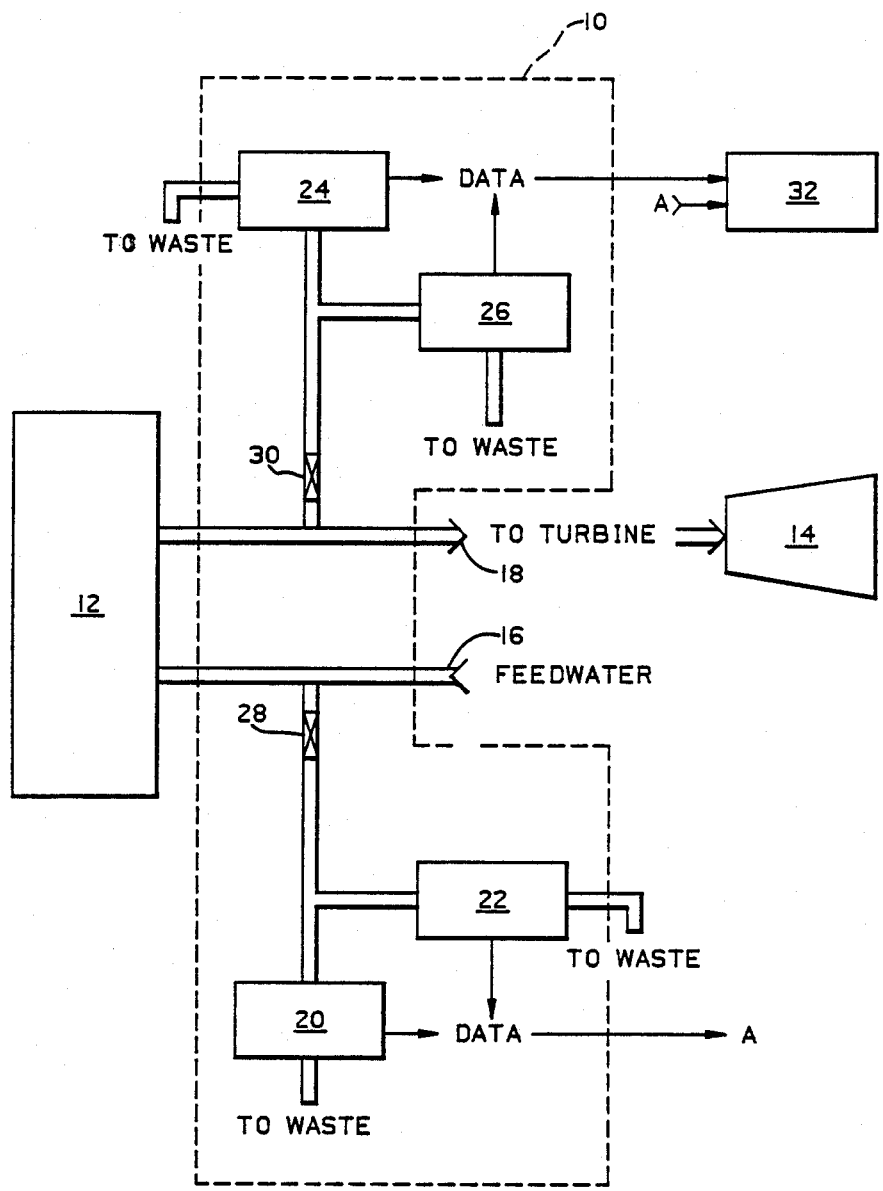
FIG. 1 is a schematic diagram illustrating application of the inventive system for detecting chlorinated organic compounds in a steam turbine system.

With reference to FIG. 1 there is illustrated an application of the novel instrumentation system 10 to the flow path of feedwater through a steam generating system 12 and into a steam turbine 14 of the type used for electric power generation. Feedwater enters the steam generator 12 through inlet piping 16 and exits through outlet piping 18 to the turbine 14. The instrumentation system 10 comprises a first hydrogen cation exchanged conductivity monitor 20 (hereinafter "cation conductivity monitor") and a first chloride monitor 22 both connected for sampling feedwater through inlet piping 16, and a second cation conductivity monitor 24 and a second chloride monitor 26 connected for sampling steam through outlet piping 18. Cut off valves 28 and 30 control fluid flow to the corresponding pairs of monitors. This system of monitors is useful for detecting the presence of chlorinated hydrocarbons in the steam generator 12, as well as for determining generally whether contaminant concentrations have increased over feedwater concentrations as a result of chemical reactions in the steam generator.

An increase in cation conductivity across the steam generator implies an increase in the number of anions in the system as water becomes superheated. The primary cause of such a gain in anion concentration is the reaction of organic compounds with hot water and steam to form acid components. Because an increase in cation conductivity across the steam generator is a definite indication of anions being generated by the reaction of organic compounds, the pair of cation conductivity monitors 20,24 provides a means for detecting organic chemicals in a power generation system and for detecting weak acids such as carboxylic acids and carbonic acid which result from the breakdown of organic matter in the steam generator 12. Similarly, if the chloride concentration in the steam is greater than in the feedwater, then chloride must have been produced in the steam generator. If the chloride results from decomposition of chlorinated organic matter then monitors 24 and 26 will indicate higher chloride levels in the steam than in the feedwater.

Normally the only source of chloride in the steam generator is organically bound chlorine. The presence of organic contaminants may be confirmed by the cation conductivity monitors 20,24. Thus the arrangement of cation conductivity monitors 20,24 and chloride monitors 22,26 forms a system of monitors for detecting contaminants, for detecting the formation of contaminants and for determining the source of contaminants in a power generation system. The above described method of monitoring provides for the detection of increased acid concentrations and distingiushes weak acids such as carboxylic acids and carbonic acid from strong acids such as hydrogen chloride by a dual monitoring technique. For example, an increase in hydrogen chloride concentration will normally be confirmed by a substantial increase in the cation conductivity. On the other hand, an increase in cation conductivity unaccompanied by a change in chloride concentration indicates only the presence of nonchlorinated hydrocarbons which have reacted with steam to form weak acids. An increase in chloride concentration without an accompanying increase in cation conductivity may suggest that increased chloride concentrations are resulting from a nonorganic source.

In a preferred embodiment of the inventive system the cation conductivity monitors 20 and 24 may take the form of a cation exchanged cartridge manufactured by Beckman Instruments, Inc., such as, for example that used in Model CH-16D, followed by a conductivity monitor manufactured by Leeds & Northrup, such as, for example, model 7076-1. The chloride monitors 22 and 26 may take the form of an ion selective electrode monitor system manufactured by Orion Research, Inc., such as, for example, Model 1517A1.

The difference in the chloride concentration between the feedwater and the steam indicates the quantity of chloride produced in the steam generator. The difference in the cation conductivity from the feedwater to the steam indicates the quantity of anions produced in the steam generator, including chloride. The amount of cation conductivity contributed by the chloride can be calculated by those skilled in the art, and thus a "corrected" cation conductivity due to organic anions and carbon dioxide may be calculated. The difference in this corrected cation conductivity between the feedwater and the steam indicates the quantity of organic anions and carbon dioxide produced in the steam generator.

The ratio of carbon dioxide to organic anions is dependent upon the temperature and configuration of the steam generator as well as the specific organic compounds entering the steam generator. In fact, it may not be necessary to convert the water to steam but only to have the exiting water at a temperature comparable to those existing in commercial electric power steam generating systems. The exact relation between the difference in corrected cation conductivity and the amount of organic compounds which have entered the steam generator must be determined by experiment for each steam generator. It may be necessary to determine this relationship periodically. The relationship can be determined from the difference in corrected cation conductivity and total organic carbon measurements in the feedwater. Total organic carbon measurement techniques are well known to those skilled in the art.

Analysis of the data may be qualitative, using only changes in quantity and direction, or it may be quantitative. Because the inventive method is based on changes in contaminant concentrations, it is not necessary that absolute concentration levels be determined. The method only requires a comparison of relative concentrations between feedwater and steam samples. In the following discussion carbon dioxide will be considered an organic anion. Qualitative analysis would determine whether organic anions underwent an increase as the water and steam passed through the steam generator and therefore whether organic compounds were present in the feedwater.

If it is determined that organic compounds have entered the steam generator through the feedwater and if the chloride ion concentration is found to rise as the feedwater passes through the steam generator, it can be concluded that the organic compounds which entered through the feedwater were chlorinated. On the other hand, if the chloride ion concentration has not increased then it can be concluded that the organic compounds which entered through the feedwater were not chlorinated. Finally, an increase in chloride ion concentration without an increase in organic anions will indicate the unlikely production of chloride ions from an inorganic material which has entered the steam generating system.

Quantitative analysis of the data will indicate how much chloride has been produced and how much organic material has entered the steam generator. From these data, the chlorine/carbon ratio can be estimated for the incoming organic compounds. Knowledge of this ratio can be helpful in determining the source of the compounds.

Figure 2A:
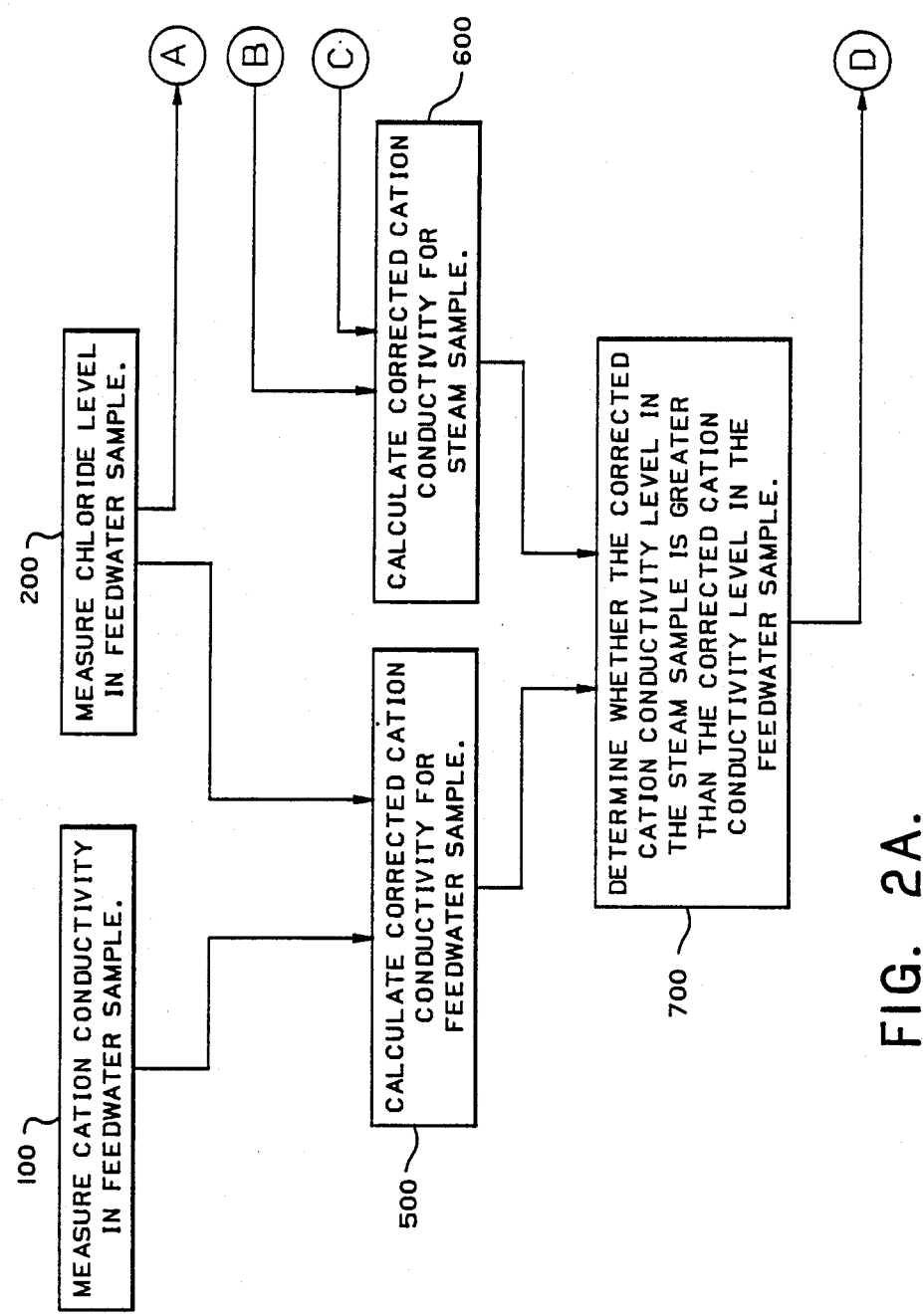
FIGS. 2A–B are flow charts illustrating a sequence of steps to be followed when implementing the inventive method.
Figure 2B:
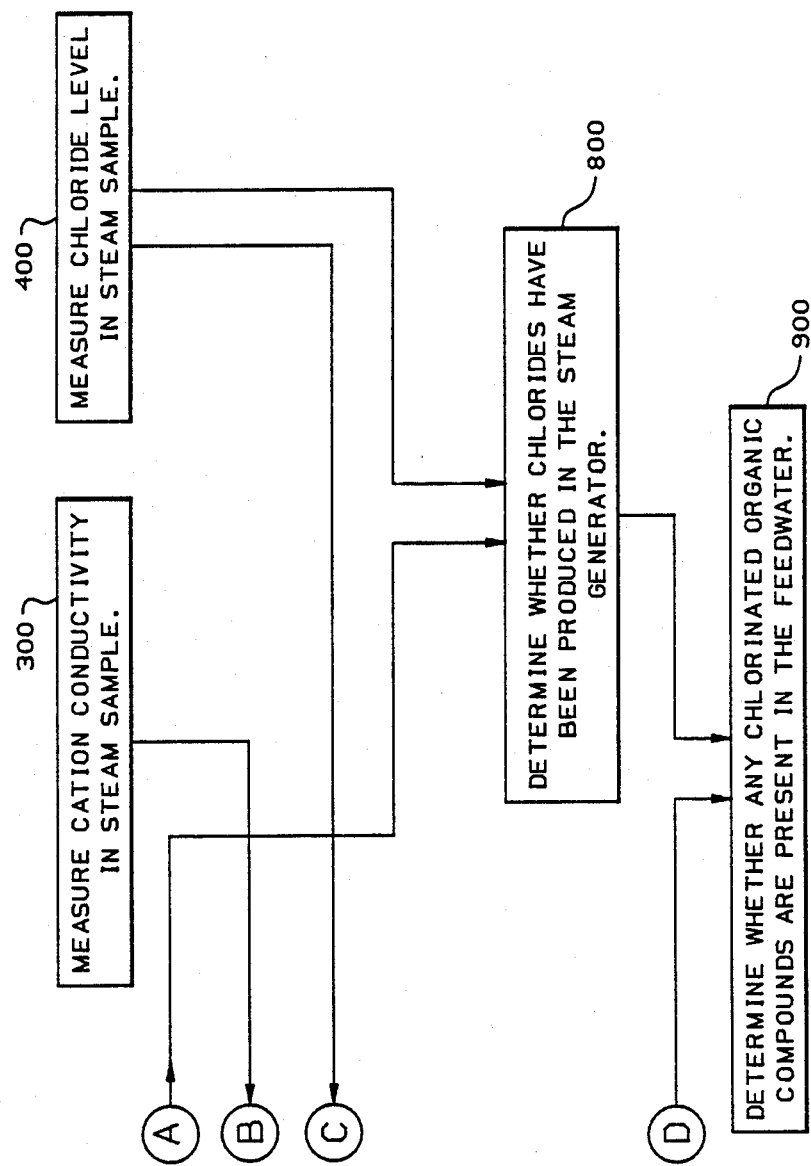

Since the reasoning involved in the analysis is complex and not always precise, the method is best implemented with a computer 32 in order to analyze various combinations of data provided by the monitors. The data may be coupled directly to the computer 32 through appropriate interfaces. The flow chart shown in FIG. 2 illustrates a preferred sequence of monitoring and analysis steps to be followed when implementing the method for detecting contaminants. Initially cation conductivity and the chloride level are measured in a feedwater sample, blocks 100 and 200. Next, cation conductivity and chloride concentration are measured in a steam sample, blocks 300 and 400. Subsequently, corrected cation conductivity levels are calculated for the feedwater and steam samples, blocks 500 and 600, and it is determined whether the cation conductivity of the steam sample is greater than the cation conductivity of the feedwater sample, block 700, wherein such increased conductivity indicates the presence of anions associated with the formation of carboxylic acids from organic compounds in the steam generator. Based on the chloride measurements, blocks 200 and 400, a comparison is made in order to determine whether any chlorides have been produced in the steam generator, block 800. Finally, based on these results, it is determined whether any chlorinated organic compounds were present in the feedwater, block 900.

It will also be apparent to those skilled in the art that the inventive method will be useful in steam generating systems for detecting the formation of other contaminants and the sources of other contaminants in addition to the contaminants so far described. Specifically, the inventive method may be applied to detect other elements present in organic compounds such as, for example, flourides, bromides, iodides, oxidized nitrogen groups and sulfur groups. Although continuous analyzers which detect contaminants in parts per billion do not currently exist for these halides and for the anions of nitrogenous and sulfurous acids, ion chromatography can be used in an on-line (continual) batch system to provide analysis of the ions in the parts per billion concentration range. Exemplary instrumentation suitable for this analysis is the Model 8000 Ion Chromatograph By Dionex, Corp. The inventive method which is applicable to these anions is had by merely replacing references made to chloride ions and monitors 22 and 26 in the previous discussions with the appropriate halogen ion, sulfate, sulfite, nitrate or nitrite ion and its respective monitors. More specifically, organic compounds in the water can be detected by appropriately heating the water to steam generator temperatures, and monitoring the water input and high temperature fluid output. The presence of anions in the system where such anions are indicative of the presence of material ions from the group consisting of flouride, iodide, bromide, nitrate, nitrite, sulfate, sulfite, phosphate and phosphite can be identified by monitoring hydrogen cation exchanged conductivity in the water input to the heater and also monitoring the hydrogen cation exchanged conductivity in the high temperature fluid exiting from the system. If the cation conductivity of the fluid sample is greater than the cation conductivity of the feedwater or water input sample, the increased conductivity is indicative of the formation of acids from organic compounds. The particular types or source of such anions in the system can then be identified by analyzing a sample of input water using ion chromatography and also analyzing a sample of the high temperature fluid using the same ion process. If the concentration of ions of a particular type in the fluid sample is substantially greater or different than the concentration of the same type of ions in the feedwater sample, such different concentration is indicative of the breakdown of corresponding compounds of flourine, bromine, iodine, nitrogen, sulfonate or phosphates.

It is also noted that the inventive method of detecting contaminants may be used in combination with a small analytical water heater or steam generator for detection and analysis of organic matter and anions of interest in water samples generally. So long as the water is heated to temperatues sufficient to form detectable anions, the high temperature fluid output of the heater can be analyzed using the inventive methods.

From the foregoing, it is now apparent that a novel method and a novel system have been presented meeting the objects set out hereinbefore as well as others, and it is contemplated that changes as to the present arrangements, details and connections of the component parts utilized in such system and method and also as to the precise steps and order thereof of such method may be made by those having ordinary skill in the art without departing from the scope of the invention as set forth in the claims which follow.

I claim:

1. A method for detecting chlorinated organic compounds in a steam generating system comprising a steam generator which receives feedwater from at least one inlet pipe and which provides steam through at least one outlet pipe, the method comprising the steps of:
    (a) monitoring chloride ion concentration in a sample of feedwater;
    (b) monitoring chloride ion concentration in a steam sample;
    (c) determining whether the chloride ion concentration in the steam sample is substantially greater than the chloride ion concentration in the feedwater sample, an increase in chloride ion concentration indicating the breakdown of chlorinated compounds;
    (d) monitoring hydrogen cation exchanged conductivity in a sample of feedwater;
    (e) monitoring hydrogen cation exchanged conductivity in a steam sample;
    (f) determining whether the hydrogen cation exchanged conductivity of the steam sample is greater than the hydrogen cation exchanged conductivity of the feedwater sample, an increase in hydrogen cation exchanged conductivity indicating the formation of carboxylic acids from organic compounds; and
    (g) determining whether hydrogen cation exchanged conductivity of the steam sample has increased relative to the feedwater sample without chloride ion concentration in the steam sample being substantially greater than chloride ion concentration in the feedwater sample, whereby nonchlorinated organic compounds in the steam generating system are indicated.

2. The method of claim 1 wherein the hydrogen cation exchanged conductivity is monitored on a relative basis and chloride ion concentration is monitored on a relative basis between the feedwater sample and the steam sample.

3. A method for detecting chlorinated organic compounds in a steam generating system comprising a steam generator which receives feedwater from at least one inlet pipe and which provides steam through at least one outlet pipe, the method comprising the steps of:
    (a) monitoring chloride ion concentration in a sample of feedwater;
    (b) monitoring chloride ion concentration in a steam sample;
    (c) determining whether the chloride ion concentration in the steam sample is substantially greater than chloride ion concentration in the feedwater sample, an increase in chloride ion concentration indicating a breakdown of chlorinated compounds;
    (d) monitoring hydrogen cation exchanged conductivity in a sample of feedwater;
    (e) monitoring hydrogen cation exchanged conductivity in a steam sample;
    (f) determining whether the hydrogen cation exchanged conductivity of the steam sample is greater than the hydrogen cation exchanged conductivity of the feedwater sample, an increase in hydrogen cation exchanged conductivity indicating the formation of carboxylic acids from organic compounds; and
    (g) determining whether both hydrogen cation exchanged conductivity and chloride ion concentration in the steam are substantially greater than in the feedwater, whereby halogenated organic compounds in the steam generating system are indicated.

4. The method of claim 3 wherein the hydrogen cation exchanged conductivity is monitored on a relative basis and chloride ion concentration is monitored on a relative basis between the feedwater sample and the steam sample.

5. A method for detecting increases in chloride ion concentration in a water heating system comprising a water heater which receives feedwater from at least one inlet pipe and which provides high temperature fluid through at least one outlet pipe, the method comprising the steps of:
    (a) monitoring chloride ion concentration in a sample of feedwater;
    (b) monitoring chloride ion concentration in a high temperature fluid sample; and
    (c) determining whether the chloride ion concentration in the high temperature fluid sample is greater than the chloride ion concentration in the feedwater sample, an increase in chloride ion concentration indicating a breakdown of chlorinated compounds.

6. The method of claim 5 wherein the chloride ion concentration of each of the feedwater sample and the high temperature fluid sample are monitored relative to one another.

7. The method of claim 5 wherein the chloride ion concentration is monitored on the basis of each of the feedwater sample and the high temperature fluid sample specific ion electrode measurements.

8. A method for detecting a presence of organic compounds and a formation of carboxylic acids in a steam generating system comprising a steam generating system comprising a steam generator which receives feedwater from at least one inlet pipe and which provides steam through at least one outlet pipe, the method comprising the steps of:
 (a) monitoring hydrogen cation exchanged conductivity in a sample of feedwater;
 (b) monitoring hydrogen cation exchanged conductivity in a steam sample; and
 (c) determining whether the hydrogen cation exchanged conductivity of the steam sample is greater than the cation conductivity of the feedwater sample, wherein an increase in hydrogen cation exchanged conductivity is indicative of carboxylic acid formation from organic compounds.

9. The method of claim 8 wherein the hydrogen cation exchanged conductivity of each of the feedwater sample and the steam sample are measured relative to one another.

10. In a steam generating system comprising a steam generator, at least one inlet pipe for providing feedwater to the generator and at least one outlet pipe for providing steam from the generator, a system for detecting the presence of chlorinated hydrocarbons in the steam generating system the improvement comprising:
 (a) first means adjacent the at least one inlet pipe for monitoring chloride ion concentration in the feedwater;
 (b) second means adjacent the at least one outlet pipe for monitoring chloride concentrations in the steam;
 (c) first means adjacent the at least one inlet pipe for monitoring hydrogen cation exchanged conductivity in the feedwater;
 (d) second means adjacent the at least one outlet pipe for monitoring hydrogen cation exchanged conductivity in the steam; and
 (e) means for comparing data from each of the monitoring means for identifying chlorinated hydrocarbons in the steam generating system.

11. A method for detecting increases in halogen ion concentration in a steam generating system comprising a steam generator which receives feedwater from at least one inlet pipe and which provides steam through at least one outlet pipe, the method comprising the steps of:
 (a) monitoring halogen ion concentration in a sample of feedwater;
 (b) monitoring halogen ion concentration in a steam sample; and
 (c) determining whether the halogen ion concentration in the steam sample is greater than the halogen ion concentration in the feedwater sample, an increase in halogen ion concentration indicating a breakdown of halogenated compounds.

12. The method of claim 11 wherein the halogen ion concentration of each of the feedwater sample and the steam sample are compared relative to one another.

13. The method of claim 11 wherein the halogen ion concentration is monitored on the basis of ion chromatography in an on-line batch system to provide analysis of the halogen ion concentration in a parts per billion concentration range.

14. A method for detecting halogenated organic compounds in a steam generating system comprising a steam generator which receives feedwater from at least one inlet pipe and which provides steam through at least one outlet pipe, the method comprising the steps of:
 (a) monitoring halogen ion concentration in a sample of feedwater;
 (b) monitoring halogen ion concentration in a steam sample;
 (c) determining whether the halogen ion concentration in the steam sample is substantially greater than the halogen ion concentration in the feedwater sample, an increase in halogen ion concentration indicating a breakdown of halogenated compounds;
 (d) monitoring hydrogen cation exchanged conductivity in a sample of feedwater;
 (e) monitoring hydrogen cation exchanged conductivity in a steam sample;
 (f) determining whether the hydrogen cation exchanged conductivity of the steam sample is greater than the hydrogen cation exchanged conductivity of the feedwater sample, an increase in hydrogen cation exchanged conductivity indicating a formation of carboxylic acids from organic compounds; and
 (g) determining whether hydrogen cation exchanged conductivity of the steam sample has increased relative to the hydrogen cation exchanged conductivity of the feedwater sample without halogen ion concentration in the steam sample being substantially greater than halogen ion concentration in the feedwater sample, whereby nonhalogenated organic compounds in the steam generating system are indicated.

15. A method for detecting organic compounds in a heating system which receives feedwater from at least one inlet pipe and which provides high temperature fluid through at least one outlet pipe, the method comprising the steps of:
 (a) identifying a presence of anions selected from the group consisting of fluoride, iodide, bromide, nitrate, nitrite, sulfate, sulfite, phosphate and phosphite, by:
  (i) monitoring hydrogen cation exchanged conductivity in a sample of feedwater;
  (ii) monitoring hydrogen cation exchanged conductivity in a high temperature fluid sample;
  (iii) determining whether the hydrogen cation exchanged conductivity of the fluid sample is greater than the hydrogen cation exchanged conductivity of the feedwater sample, an increase in hydrogen cation exchanged conductivity indicating a formation of acids from organic compounds; and
 (b) identifying the source of such anions in the system by:

(i) analyzing a sample of feedwater using ion chromatography;
(ii) analyzing a high temperature fluid sample using ion chromatography;
(iii) determining whether a concentration of anions of a particular type in the fluid sample is substantially different than the concentration of the same type of anions in the feedwater sample, whereby a breakdown of compounds of fluorine, bromine, iodine, nitrogen, sulfonate or phosphates corresponding to the anions is indicated.

* * * * *